United States Patent [19]

Romelli et al.

[11] 4,225,574
[45] Sep. 30, 1980

[54] METHOD FOR DETERMINATION OF FREE HORMONES IN BIOLOGIC FLUIDS

[75] Inventors: Pier B. Romelli, Rho; Francesco Pennisi, Milan, both of Italy

[73] Assignee: Gruppo Lepetit S.p.A., Milan, Italy

[21] Appl. No.: 880,411

[22] Filed: Feb. 23, 1978

[30] Foreign Application Priority Data

Mar. 10, 1977 [IT] Italy ............................... 21128 A/77

[51] Int. Cl.$^2$ ...................... G01N 33/16; A61K 43/00
[52] U.S. Cl. ...................................... 424/1; 23/230 B; 424/12
[58] Field of Search ..................... 23/230 B; 424/1, 12

[56] References Cited

U.S. PATENT DOCUMENTS

| 4,020,151 | 4/1977 | Bouz et al. | 424/1 |
| 4,046,870 | 9/1977 | Hertl et al. | 424/1 |

Primary Examiner—Benjamin R. Padgett
Assistant Examiner—Christine M. Nucker

[57] ABSTRACT

A method for direct determination of the free fraction of an hormone in a biological fluid containing bound and unbound hormone in an equilibrium state. A fluid sample is contacted with a solid matrix capable of reversibly binding the free hormone without sensibly affecting the equilibrium state and the amount of adsorbed hormone is determined and directly correlated with the free hormone in the biological fluid. The method is particularly suitable for direct determination of free thyroxine and triiodothyronine in serum.

11 Claims, No Drawings

METHOD FOR DETERMINATION OF FREE HORMONES IN BIOLOGIC FLUIDS

BACKGROUND OF THE INVENTION

It is known that some of the hormones circulating in the body fluids show two forms: one is bound to carrier proteins and the other is unbound. The two fractions are in an equilibrium state between themselves and the free fraction is, in many cases, directly responsible of the biological effects. In particular, thyroid hormones, thyroxine (T4) and triiodothyronine (T3) circulating in the blood are mainly bound to carrier proteins by a non-covalent binding. Carrier proteins include an $\alpha$-globulin (thyroxine-binding globulin, TBG), binding about 75% of the hormones, a pre-albumin fraction (TBPA) and an albumin fraction (TBA) binding about 15% and 10% of the hormones, respectively. The association constants of T3 and T4 with binding proteins are different: T3-TBG association constant is lower than T4-TBG association constant, T3-TBPA association constant is negligible. Even if very small fractions of T3 and T4 circulate unbound in plasma (FT3 and FT4), only unbound fractions are thought to be biologically active. Evidence has been given that bound hormone fractions cannot pass through cell membranes.

It is therefore essential to correlate the hormone functions with its free fraction rather than with its total amount present in the serum. Variations of the free fractions observed in hypo- and hyperthyroid subjects, are more closely correlated to clinical symptoms than those found for total thyroid hormones. Free fractions levels of hypo- and hyperthyroid subjects do not overleap values of euthyroid subjects, as observed for total hormones level. Therefore, free fraction measurements avoid doubtful diagnostic evaluations occuring in "border-line" zones.

The determination of free T3 and T4 discloses new interesting studies in non thyroidal diseases. For example, an increase of free T4 level is observed in patients affected by angina pectoris. In addition, as free thyroid hormones levels, and particularly free T3level, play an important role in maintaining the homeostasis of hypothalamo-pituitary-thyroid system, a more extensive evaluation of this role in physiological and pathological conditions can be performed.

Interaction between thyroid hormones and binding proteins can be described by a reversible reaction, to which the mass action law can be applied: the equilibrium between the unbound (free) and the bound hormone fraction depends on the association constant of each binding protein and on the number of binding sites. Circulating hormone-protein complexes can be considered as reservoir system to avoid sharp variations of thyroid secretory activity. About 0.01 to 0.04 percent of the total amount of T4 and 0.2 to 0.4 percent of the total amount of T3 are unbound. With regard to hormones capable of binding to serum proteins, for each species of binding site the situation is represented by the following equilibrium

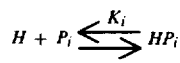

wherein H is the concentration of the free hormone, $P_i$ is the concentration of the free sites of type i, $HP_i$ is the concentration of the bound sites of type i and $K_i$ is the relative association constant.

In this case the concentration of the free hormone is $$H = \frac{HP_i}{K_i \cdot P_i} = \frac{HP_i}{K_i(M_i - HP_i)}$$

wherein $M_i$ is the total concentration of bound and non-bound sites of type i. Since the binding sites of a single protein may be of different type as well as the proteins present in the whole system, in a more general way, in the case of n species of binding sites in the serum, the situation at the equilibrium conditions is represented by the following relationship $$H = \frac{\sum_{i=1}^{n} HP_i}{\sum_{i=1}^{n} K_i(M_i - HP_i)}$$

wherein H is the concentration of the circulating free hormone, $M_i$ and $HP_i$ are as described above and the summations refer to the species of binding sites i in the serum and to the relative association constants toward the hormone.

TBG and TBPA have a single binding site per molecule while albumine has two binding sites with different association constant.

The concentration of a free hormone in a biological fluid is usually determined by multiplying its free fraction percent by the amount of total hormone present in the fluid. Said percentage may be determined, for instance, through dialysis of the serum mixed with a known amount of labelled free hormone. This method applied to thyroxine (T4) is, for instance, described by S. H. Ingbar et al. in J. Clin. Invest. 44, 1679, (1965). However, it does not yield very reliable results since there are several factors which may affect the result such as the presence of $I^{125}$ ions which negatively influences the calculation of the fraction of bound hormone to non-bound hormone.

The direct method provided by S. Ellis and R. Ekins (Acta Endocrinologica Suppl. 177, 106, 1973-IX Acta Endocrinologica Congress, Oslo June, 17-21, 1973) for the determination of thyroxine and triiodothyronine requires a good technical experience which is generally not common among the technicians who carry out these kinds of analysis as the method is rather complicated. Also this method is based on dialysis procedures.

In the specific case of T4, two further approaches have been studied. The first one(free T4 index)is based on the determination of the total T4 serum level (according for instance to U.S. Pat. No. 3,659,104) and on the T3 uptake (according, for instance, to U.S. Pat. No. 3,710,117). The second one is based on the complete dissociation of T4 in the presence of labelled T4, followed by absorption on a resin and elution of labelled T4 from the resin by means of a portion of the serum under examination (U.S. Pat. No. 3,941,564).

By using the first approach, the arithmetic product of the T4 total serum level and the T3 uptake is an indirect extimate of free T4. (free T4 index). This extimate is better correlated to the thyroid functionality; however two separated tests are necessary with a magnification of the errors. Both methods, yield an indirect value of free T4. With these methods no information can be obtained about free T3.

For the reasons given above it is evident that only a direct measurement of free T3 and T4 has greater possibility to be utilized for diagnostics purposes.

SUMMARY OF THE INVENTION

This invention relates to a method for the direct determination of the free hormone fractions in biological fluids. In particular this invention relates to a simple and quick procedure for the determination of free T3 and T4 in serum. (FT3 and FT4).

It was found that where a sample of serum containing said hormones is contacted (preferably after dilution with a buffer to stabilize the pH) with a solid matrix capable of selectively and reversibly binding the free hormones and perturbing the above described equilibrium, the concentration of the free fractions of said hormones may be easily determined by measuring the hormone amounts bound to the solid matrix and by dividing the obtained values by a factor ($\phi$) which is related to the physical characteristics of the solid matrix.

It is obvious that said determination is possible only if the solid matrix perturbs the equilibrium governing the system only to a small extent. For instance, the variation of the free hormone fractions due to the perturbation must be in any case lower than 10%.

According to this invention, it was found that by appropriately selecting the type of solid matrix and its amount in respect to the volume of the serum sample, (after dilution with the buffer), the above described conditions are met.

In particular, it was found that said direct determinations of free hormone fractions are possible when a binding solid matrix is selected having an absorption constant $K_s$ toward the hormones very low and a total number of binding sites $S_o$ very high in comparison with the number of binding sites actually bound to the hormone adsorbed (H S).

It was definitely shown that for a satisfactory determination of the free hormones in a system such as the one represented by the above equilibrium, the value of the product $D.K_s.S_o$ must be equal or less than 10% of the value of the summation $$\sum_{i=1}^{n} K_i(M_i - HP_i)$$

where D is the dilution factor whereby the serum sample is diluted before being contacted with the solid matrix, $K_s$ is the absorption constant of the matrix toward the free hormone, $S_o$ is the total number of binding sites of the solid matrix and $$\sum_{i=1}^{n} K_i(M_i - HP_i)$$

is the summation of the products of the association constants $K_i$ of the binding sites of type i and the concentrations ($M_i - HP_i$), defined as above, of the unbound binding sites of type i for all n species of binding sites in the serum.

When the above operative conditions are met the amount of hormone bound to the solid matrix is correlated in a direct proportional way to the concentration of the free hormone originally present in the biological fluid.

Solid matrices suitable for selective and reversible absorption of the free hormones form biological fluids may be selected from substances of various type such as for example, the synthetic resins, the solid natural polymers, such as starch, dextran and the same natural polymers modified by chemical or physical treatment. Although it is not essential to the scope of the invention, it is preferred to use solid matrices which allow an easy and complete recovery of the adsorbed hormones, by means, for instance, of elution with a solvent. It was found that commercial synthetic or modified resins may be advantageously employed provided the ratio of the resin amount to the volume of the test sample is appropriately determined. Example of commercial synthetic or modified resins are for instance those sold under the trade names Sephadex ®, Sepharose ®, Amberlite ® and Dowex ®.

As a guidance for the selection of the solid matrices, the value of the summation $$\sum_{i=1}^{n} K_i(H_i - HP_i)$$

can be calculated by substituting the values of $K_i$, $M_i$ and $HP_i$ reported by various authors for specific systems such as, for instance, for carrier proteins of T3 and T4 in serum.

The values of the product $K_s S_o$ can be calculated or experimentally determined for each matrix taken into consideration by using the following relationship between the known concentration of the free hormone in a standard sample and the amount of hormone HR bound to the matrix after contact with said standard sample:

$$H = HR/\phi$$

wherein $\phi$ is equal to the product $K_s S_o$.

In the case of the determination of the free hormones T3 and T4 (FT3 and FT4) highly satisfactory results are obtained with the use of modified polysaccharides such as for instance Sephadex G-25 ®(a modified dextran wherein the macromolecules are cross-linked) or Sephadex LH-20 ® (a bead-formed hydroxypropylated dextran gel where the polysaccharides chains have been cross-linked to give a three-dimensonal network). In this case, the resin is employed in such amount that the product $K_s S_o$ results to be of about 10 to about 80. The value of the factor D may be in general maintained in the range from about 1 to about 20, selecting for each hormone the appropriate value.

According to an embodiment of the invention, a sample of a preferably fresh or well preserved biological fluid containing the free hormone to be determined is added with a buffer solution to have a final pH value ranging between 7.3 and 7.8. The volume of the buffer added is about equal to that of the serum sample. The solution thus obtained is contacted with a predetermined amount of an appropriately selected solid matrix at a physiologically acceptable temperature. When the equilibrium perturbed by the presence of the solid matrix is stabilized, the residual liquid is removed and the matrix is repeatedly washed with a buffer pH 7.3 to 7.8 to eliminate any trace of the solution text sample. The hormone adsorbed on the matrix is eluted with a solvent such as, for instance, methanol. The methanol eluate is then evaporated and the residual hormone is determined by a common analytical method.

In general, the most suitable analytical method for these determinations is the radioimmunoassay. For instance, in the case of thyroid hormones, the method described by F. Pennisi et al. (Quaderni Sclavo di Diagnostica 197, Vol. 11, page 311) may be advantageously employed.

The amount of hormone bound to the matrix (HR) is correlated to the free hormone present in the serum (H) through the following relationship $$H = HR/\phi, \quad (\phi = K_s S_o)$$

wherein $\phi$ (adsorption factor) is a factor depending on the physical characteristics of the solid matrix which may be experimentally determined, or in some instances, theoretically calculated on the basis of literature data.

DESCRIPTION OF THE PREFERRED EMBODIMENTS

To give an example of the preferred mode to perform the method of the invention, the procedure followed for the determination of the FT4 in serum is herein described in details.

A sample of 0.5 ml of serum is introduced, through the upper opening, into a chromatographic column having an inside diameter of 10 mm and a length of 70 mm. The column is divided in two sections and has two terminal openings with their respective caps. The lower opening has a smaller diameter. In the upper section are contained 0.5 ml of a buffer solution pH 7.3(0.1 M. phosphate).

In the lower section is contained the solid matrix equilibrated with the same buffer. The matrix is retained between two porous polyethylene discs. The solid matrix consists of 150 mg of Sephadex LH-20.

The solution obtained by mixing the serum with the buffer is carefully shaked and then the fluid in excess is removed through the lower opening.

After removal of the liquid the column is stopped with caps. The column containing the solid matrix inbibed with residual liquid is incubated for one hour at 37°±2° C.

The column is then washed twice with 2 ml of buffer solution pH 7.4 (0.1 M. tris(hydroxymethyl)aminomethane hydrochloric acid) at 37°±2° C. and once with 0.4 ml of methanol to remove the residual buffer solution. The washing liquids are discarded. The hormone adsorbed on the solid matrix in the column is then eluted with 2 ml of methanol. The eluate is collected in a test tube and then evaporated to dryness under vacuum in a thermostat at 37° C.

The sample thus obtained is then submitted to radioimmunological assay. The following procedure is followed for the dosage of free T4.

Besides the test sample, other six standard samples are submitted to radioimmunological dosage. These samples are prepared with essentially the same procedure as the one described for the test sample by using predeterminated amounts of hormone T4. In these standard samples are employed 0, 60, 120, 240, 480 and 720 picograms respectively of hormone T4. Standard samples are prepared also for T3 dosage when concomitant radioimmunological assays are to be performed on a single serum sample. The radioimmunological assay is preferably carried out on double samples prepared by adding to each standard sample and to the text sample 4 ml of buffer solution pH 7.4 and transferring portions of 0.5 milliliters of each of the thus obtained solutions into two test tubes. To each of these tubes is added 0.1 ml of an aqueous solution containing a predetermined amount of T4-I[125]. With the labelled product (0.1 ml) and with the buffer (0.6 ml) are moreover prepared two sample for the total activity count and for the blank.

To all test tubes, except the latter couple, is added 0.1 ml of water solution containing a predetermined amount of T4 antiserum. All tubes, each containing 0.7 ml of liquid, are then incubated for four hours at 4° C. The hormone bound to the antibody is then separated from the unbound hormone by addition to each tube of 0.5 ml of a suspension of charcoal/dextrane in distilled water (charcoal 20 mg/ml, dextrane 2 mg/ml, $\gamma$ glubuline 3 mg/ml in phosphate buffer pH 7.4) followed by centrifugation at 4000 r.p.m. for 15 minutes. The charcoal is added also to the tubes which do not contain antiserum. The surnatant liquid of each tube is transferred in a new series of tubes for the radioactivity count. In the case of the tubes prepared for the total activity count and for the blank (those not containing the T4-antiserum) it is submitted to count also the charcoal precipitated by centrifugation.

The tubes containing the surnatant liquid are submitted to radioactivity count on calculating the arithmetical mean for each couple.

The radioactivity of the tubes which do not contain antiserum corresponds to the radioactivity present in the surnatant liquid also in the absence of the antibody(-blank).

These counts are due to small amounts of substances immunologically inactive and must be subtracted from the mean counts of each pair of tubes to obtain the corrected mean value. The radioactivity of the precipitated charcoal corresponds to the total radioactivity added to the tubes (total activity count). These values are useful for controlling the quality of the reagents and the operative technique.

With the corrected mean counts obtained from the pairs of standard and test tubes are defined the values of the reciprocal competition ratio (R.C.R.) for all standard and test samples. The R.C.R. values corresponds to the ratio between the corrected mean count of the standard pair of tubes which do not contain any amount of T4 (standard O) and the corrected mean count of each of the other pairs of standard and test samples.

There are thus obtained several R.C.R. values which refer to the several standard and test samples and which may be correlated with their respective original contents of T4 through a linear relationship of the type: $y = a + bx$ wherein y is the R.C.R. value and x is the hormone amount absorbed by the matrix expressed in picograms.

The concentration of FT4 in the original text sample is therefore determined by reading the value of x for the corresponding value of y obtained as described above and dividing it by the factor $\phi$.

For the determination of FT3 in serum essentially the same procedure is followed.

Comparison tests have been made between the method involving dialysis (Ellis and Ekins) and the method of this invention by using the same heterogeneous groups of patients. Statistical tests applied to comparison studies (linear regression analysis and Student's t "paired test") show that the results obtained using the two methods are not significantly different. The following table summarizes the results:

FT3 AND FT4 ASSAY: COMPARISON OF RESULTS OBTAINED USING THE DIALYSIS METHOD (x) AND THE METHOD OF THIS INVENTION (y)

| ASSAY | No. | Linear regression analysis | | | | Paired t-test | | | |
|---|---|---|---|---|---|---|---|---|---|
| | | a pg/ml | b | S pg/ml | r | Bias pg/ml | (SD) pg/ml$^d$ | t | t 0.05 |
| FT3 | 81 | 0.703 | 0.848 | 0.610 | 0.947 | −0.038 | 0.684 | 0.503 | 1.9901 |
| FT4 | 55 | 0.463 | 0.968 | 1.691 | 0.910 | −0.151 | 1.700 | 0.658 | 2.0049 | n = number of assays
x = results obtained using dialysis method;
y = results obtained using the invention method
Linear regression analysis:
y = a + bx,
$S_y$ = standard error of estimate;
r = coefficient of correlation of linear regression
t-test:
d = (x − y);
$SD_d$ = standard deviation of differences $$Bias = \frac{\Sigma d}{n};$$

$$t = \frac{Bias}{\frac{(SD)d}{\sqrt{n}}}$$

We claim:

1. A process for determining the concentration of the free fraction of a hormone in a biological fluid containing bound and unbound hormone in an equilibrium state which comprises contacting a sample of the biological fluid with a solid matrix capable of reversibly selectively adsorbing the free hormone, whereby the equilibrium between the bound and unbound fraction of the hormone remains substantially undisturbed and determining the amount of hormone bound to said solid matrix directly correlating the adsorbed hormone with the concentration of the free hormone present in said body fluid.

2. A method as in claim 1 wherein the hormone bound to the solid matrix is correlated to the free hormone present in the biological fluid by the following relationship $H = HR/\phi$, wherein H corresponds to the concentration of free hormone fraction in the sample of biological fluid contacted with said matrix, HR is the amount of hormone bound to the matrix and $\phi$ is a factor related to the physical characteristics of the solid matrix.

3. A method as in claim 1 wherein the value of the product $DK_sS_o$ is equal or lower than 10% of the value of the summation $$\sum_{i=1}^{n} K_i(M_i - HP_i)$$

wherein D is the dilution factor whereby the biological field is diluted before being contacted with the solid matrix, $K_s$ is the absorption constant of the solid matrix toward the free hormone, $S_o$ is the total number of binding sites in the solid matrix and $$\sum_{i=1}^{n} K_i(M_i - HP_i)$$

is the summation of the products of the association constant $K_i$ of the binding sites of type i toward the hormone and the concentration $(M_i-HP_i)$ of the unbound sites of type i, $M_i$ being the total concentration of the sites of type i and $HP_i$ the concentration of the bound sites of type i, for all n species of binding sites in the biological fluid.

4. A method as in claim 1 wherein the biological fluid is blood serum and the contact between the blood serum and the solid matrix is carried out at stabilized pH ranging between 7.3 and 7.8 at a physiologically acceptable temperature.

5. The method of claim 1, 2 or 3 wherein the hormone is thyroxine and/or triiodothyronine.

6. A method of claim 5 wherein the value of the product $K_sS_o$ ranges between about 10 and about 80 and the value of D ranges between about 1 and about 20.

7. The method of claim 1, 2, 3, or 4 wherein the analytical method for determining the hormone bound to the solid matrix is a radioimmunological method.

8. A method of claim 1 wherein the solid matrix is selected from natural, synthetic or modified resins.

9. A method of claim 1 wherein the solid matrix is selected from the modified tridimensional polysaccarides.

10. A method of claim 1 wherein the solid matrix is Sephadex LH-20.

11. A method of claim 1 wherein the solid matrix is Sephadex G-25.

* * * * *